United States Patent [19]

Chang

[11] Patent Number: 5,543,144
[45] Date of Patent: Aug. 6, 1996

[54] TREATING HYPERSENSITIVITIES WITH ANTI-IGE MONOCLONAL ANTIBODIES WHICH BIND TO IGE-EXPRESSING B CELLS BUT NOT BASOPHILS

[75] Inventor: Tse W. Chang, Houston, Tex.

[73] Assignee: Tanox Biosystems, Inc., Houston, Tex.

[21] Appl. No.: 7,180

[22] Filed: Jan. 21, 1993

Related U.S. Application Data

[63] Continuation-in-part of Ser. No. 357,483, May 26, 1989, Pat. No. 5,420,251, which is a continuation-in-part of Ser. No. 291,068, Dec. 28, 1988, abandoned, which is a continuation-in-part of Ser. No. 226,421, Jul. 29, 1988, Pat. No. 5,422,258, which is a continuation-in-part of Ser. No. 140,036, Dec. 31, 1987, abandoned.

[51] Int. Cl.$^6$ .................... A61K 39/395; C07K 16/42
[52] U.S. Cl. .................... 424/133.1; 424/139.1; 424/145.1; 530/387.3; 530/388.25
[58] Field of Search .................... 424/85.8; 530/387.3, 530/388.25; 435/240.27, 172.2, 70.21

[56] References Cited

U.S. PATENT DOCUMENTS

| | | |
|---|---|---|
| 4,161,522 | 7/1979 | Hamburger . |
| 4,171,299 | 10/1979 | Hamburger . |
| 4,536,479 | 8/1985 | Vander-Mallie . |
| 4,683,292 | 7/1987 | Hahn . |
| 4,714,759 | 12/1987 | Whitaker, Jr. . |
| 4,940,782 | 7/1990 | Rup et al. ............ 530/388.25 |
| 5,180,805 | 1/1993 | Gould et al. . |

FOREIGN PATENT DOCUMENTS

| | | |
|---|---|---|
| WO88/00204 | 1/1988 | WIPO . |
| 8906138 | 7/1989 | WIPO . |
| 9007861 | 7/1990 | WIPO . |
| 9109967 | 7/1991 | WIPO . |

OTHER PUBLICATIONS

Bozelka et al., Immunology 46:527–532 (1982).
Haba & Nisonoff, Proc. Nat'l Acad. Sci. USA 84:5009–13 (1987).
Haba & Nisonoff, J. Exp. Med. 168:713–724 (1988).
Haba et al., J. Immunol. Methods 73:97–108 (1984).
Haba & Nishonoff, J. Immunol. Methods 85:39–52 (1985).
Haba et al., J. Immunol. 134:3291–97 (1985).
Morrison, Science 229:1202–1206, 1985.
Hook, W. A. et al. "Monoclonal Antibodies Defining Epitopes on IgE Fed. Proc." 46:1346 (1987).
Hook, W. A. et al. "Histamine Release by Structural Analogs of LNRH" Fed. Proc. 44:1323 (1985).
Hook, W. A. et al. "Differential Binding by mAbs to Fluid Phase vs. Basophil–Bound IgE" Clinical Research 33:515A (Apr. 1985).
Hook, W. A. et al. "Detection of Different Antigenic Sites on Human IgE Using Monoclonal Antibodies" Fed. Proc. 42:713 (1983).
Hook, W. A. et al. "Monoclonal Antibodies to Human IgE" Fed. Proc. 40:965 (1981).
Hook, W. A. et al. "Heterogeneity of Monoclonal Antibodies which Bind Unheated or Heated Human IgE" Fed. Proc. 41:825 (1982).
Baniyash, M et al. "Relationships Between Epitopes on IgE Recognized by Defined mAbs and by the Fc Receptor on Basophils" J. Immunol. 136:588–592 (1986).
Baniyash, M. et al. "Inhibition of IgE binding to mast cells and basphils by monoclincal antibodies to murine IgE" Eur. J. Immunol. 14:799–807 (1984).
Stanworth and Burt, Molec Immun. 23:1231–1235 (1986).
Shulman et al., Nature 276: 269 (1978).
Roberts et al., Nature 328:731–734 (1987).
Lin and Putnam, Proc. Natl. Acad. Sci. USA, 78:504–508 (1981).
Ishida et al., EMBO J. 1117–1123 (1982).
Stanworth, Molec. Immun., 21:1183–1190 (1984).
Baniyash and Eshhar, Eur. J. Immunol. 17: 1337–1342 (1987).
Mayworth, "Designing Antibodies", Academic Press Inc., 1993, pp. 61–63.
CAS Abstract No. 121:106525, Washida et al., EP592230, 1994 21 pp.
CAS Abstract No. 119:247986, Whitaker, WO9319197, 1993, 52 pp.
Barbas et al. PNAS USA 90:10003–10007 Nov. 1993.
Casali et al., Science 234:476–479, 1986.
Baniyash, "Immunochemical/Characterization of the Interaction between Immunoglobulin E and its Receptor", Dcotur/Thesis, May 1986.
Queen et al. PNAS 86:10029–10033, 1989.
Waldmann, Science 252:1657–1662, 1991.
Harris et al. Tibetech 11:42–44, 1993.

Primary Examiner—Paula K. Hutzell
Attorney, Agent, or Firm—Eric P. Mirabel

[57] ABSTRACT

The invention relates to methods of treating allergic reactions and of reducing circulating IgE using antibodies which bind to secreted IgE and membrane-bound IgE on the surface of IgE-producing B cells but not to IgE on basophils or mast cells.

6 Claims, No Drawings

TREATING HYPERSENSITIVITIES WITH ANTI-IGE MONOCLONAL ANTIBODIES WHICH BIND TO IGE-EXPRESSING B CELLS BUT NOT BASOPHILS

RELATED APPLICATIONS

This application is a continuation-in-part of U.S. application Ser. No. 07/351,483, filed May 26, 1989 and now U.S. Pat. No. 5,420,251, which is a continuation-in-part of U.S. application Ser. No. 07/291,068 (abandoned), filed Dec. 28, 1988, which is a continuation-in-part of U.S. application Ser. No. 07/226,421, filed Jul. 29, 1988 and now U.S. Pat. No. 5,422,258, which is a continuation-in-part of U.S. application Ser. No. 07/140,036 (abandoned), filed Dec. 31, 1987.

FIELD OF THE INVENTION

The invention relates to anti-IgE monoclonal antibodies which bind to IgE-expressing B cells but do not bind to basophils or mast cells, and their use in treating hypersensitivities such as allergies.

BACKGROUND

The immediate-type hypersensitivities, such as extrinsic asthma, hay fever, and allergic responses to certain food or drags, are mediated primarily by immunoglobulin E (IgE). In an IgE-mediated allergic response, the allergen binds to IgE on the surface of mast cells and basophilic leukocytes (basophils). This binding causes a crosslinking of the IgE molecules, and the underlying receptors of the mast cells or basophils for the Fc potion of IgE (FcεR), and triggers the release of pharmacologic mediators such as histamine, the slow-reacting substance of anaphylaxis, and serotonin. The release of these mediators causes the various pathological manifestations of allergy.

Patients affected with allergies or other IgE-mediated hypersensitivities are often treated with histamine antagonists ("anti-histamines") to alleviate symptoms. In addition, during hay fever seasons, desensitization procedures are used to prevent or alleviate allergic reactions. In these procedures, small doses of allergen are injected periodically to induce certain immune responses that may reduce the IgE-mediated responses. Desensitization procedures are more effective in some patients than in others.

It has been suggested that IgE-mediated hypersensitivities might be treated by inhibiting the binding of IgE to mast cells and basophils. For example, synthetic peptides representing various regions of the Fc of IgE (Fcε) have been explored as competitive inhibitors for the binding of IgE to the receptors on mast cells and basophils. See e.g., Stanworth, D. R., *Molec. Immun.* 21:1183–1190 (1984); Stanworth, D. R. and Burt, D. S., *Molec. Immun.* 23:1231–1235 (1986); Burt, D. S. et al., *Molec. Immun.* 24:379–389 (1987); Hahn, U.S. Pat. No. 4,683,292: Hamburger, U.S. Pat. Nos. 4,171,299 and 4,161,522. However, presumably due to the fact that the affinity of these peptides for FcεR is lower than for whole IgE, such peptides have not been proved very effective for treatment of allergy.

In recent years, monoclonal antibody methodologies have been employed to map the various antigen and functional epitopes on IgE. Baniyash and Eshhar (*Eur. J Immunol.* 14:799–807 (1984)) reported that among the several rat monoclonal antibodies made against IgE, three inhibited the binding of mouse IgE to rat basophils cells. Since the antibodies could also induce serotonin release from basophils bound with IgE, the antibodies probably bound sites on Fc which were near but not in the site binding to the receptors for IgE on basophils. More recently the same investigators developed a monoclonal antibody that could inhibit the binding of the IgE to basophils but does not recognize IgE on basophil surface. Baniyash et al., *Molec. Immunol.* 25:705 (1988). Siraganian et. al. (see Fed. Proc. 40:965 (1981), *Fed. Proc.* 46:1346 (1987)) reported that among approximately ten mouse monoclonal antibodies made against human IgE, a few did not bind IgE on basophils, and that some of these could inhibit the binding of human IgE to basophils. These studies were directed to the use of monoclonal antibodies to define the various epitopes or functionally related peptidic segments on IgE.

U.S. Pat. No. 4,714,759 describes an immunotoxin specific for the IgE isotype and its use in the treatment of allergy. The immunotoxin comprises an anti-IgE antibody coupled to a toxin. The concept behind the treatment is that the immunotoxin specific for IgE binds to IgE on IgE-producing B cells and kills them. However, the immunotoxin would also bind to IgE on basophils and mast cells, which could lead to anaphylaxis and possibly result in death.

SUMMARY OF THE INVENTION

This invention relates to anti-IgE monoclonal antibodies and related products which bind secreted IgE and IgE-expressing B cells, but do not bind to basophils or mast cells. The invention further relates to methods of treating IgE-mediated hypersensitivities with these monoclonal antibodies and related products.

Although IgE is produced only by B cells which also express IgE on their surface ("IgE-expressing B cells"), it is also present on mast cells and basophils. IgE has a very high affinity for the FcεR on the surface of basophils and mast cells (the association constant, Ka, is in the range of $10^9$–$10^{10}$ liter mole$^{-1}$) and the rate of dissociation is very slow (the half life or "on time" is about 20 hours). Thus, IgE is virtually always present on the surface of basophils and mast cells.

The epitopes on IgE bound by the monoclonal antibodies and related products of this invention are present on IgE-expressing B cells but not on basophils or mast cells and are, therefore, unique surface markers of IgE-expressing B cells. These epitopes are referred to hereinafter as ige.bl (bl denotes B lymphocytes).

There are two distinct forms of IgE: the membrane-bound form and the secreted form. The IgE on IgE-expressing B cells is the membrane-bound form, and is anchored on the membrane by an extra segment extending from the C-terminal end of the molecule which spans through the membrane lipid bilayer. The structures of the two forms of IgE are different, in that the membrane-bound form has this extra segment. The IgE on basophils and mast cells is the secretory form and is anchored to the basophil and mast cell surface through the immunoglobulin Fc portion binding to the Fcε receptors on the basophils and mast cells.

One class of ige.bl epitopes is located in the Fc region of the IgE molecule at or near the binding site of FcεR. Another class of ige.bl epitopes are antigenic epitopes located on extracellular segment of the membrane-bound region of membrane-bound immunoglobulin heavy chains. In general, these can be designated mb/ec. The mb/ec segment of IgE is designated as the ε.mb/ec segment. Reagents which specifically bind to these epitopes and their use in therapy are described in U.S. Pat. Nos. 5,091,313; 5079,344; 5,089,603, the teachings of which are incorporated by reference herein.

Monoclonal antibodies (and related products such as antibody fragments and immunotoxins) which bind to ige.bl epitopes allow therapy and diagnosis of various IgE-mediated hypersensitivity, including allergic diseases such as extrinsic bronchial asthma, allergic rhinitis or hay fever, and food and drug allergies. For purposes of the therapeutic methods of this invention, the specific binding agent can be any molecule which specifically binds to the ige.bl epitopes (and thus binds to IgE-expressing B cells but not basophils). These reagents include peptides which are identical or analogous to the antigen binding region (variable of hypervariable regions) of anti-ige.bl antibodies. Although the description below focuses mainly on anti-ige.bl monoclonal antibodies and related products, the concept and methodologies are equally applicable to other molecules specific for the unique epitopes described herein.

Monoclonal antibodies (and related products such as antibody fragments and immunotoxins) specific for an ige.bl epitope can be used to selectively destroy IgE-producing cells. Because the epitope is present on IgE-expressing B cells and not on mast cells or basophils, monoclonal antibodies specific for an ige.bl epitope bind B cells, but not mast cells or basophils. This differential binding allows the targeting and selective elimination of IgE-producing B cells. The preferred monoclonal antibodies and related products also have the additional property of not binding IgE bound to the CD23 receptor on B cells, or of inhibiting binding to the CD23 receptor.

The monoclonal antibodies and related products which are specific for the ige.bl epitope at or near the FcεR site of binding to IgE may also have additional therapeutic effects. They bind IgE and form immune complexes, thereby facilitating the removal of IgE from the immune system by the reticuloendothelial system.

The invention also relates to dectecting IgE or IgE-bearing B cells in an unknown fluid sample with antibodies or related products of the invention. The antibodies can be used in standard assay formats, such as ELISAs, for this purpose.

This invention also relates to paratope-specific, antiidiotypic antibodies to the antibodies reactive with ige.bl epitopes, to peptides which are modeled after the epitopes (e.g., the site of FcεR binding), to the use of the antiidiotypic antibodies and the peptides to treat IgE-mediated allergic diseases, and the use of these peptides and antiidotypes in screening for the monoclonal antibodies of the invention. The invention also relates to immunotoxins formed of antibodies which react with the ige.bl epitopes and a toxin, such as the ricin A chain or pseudomonas exotoxin.

DETAILED DESCRIPTION OF THE PREFERRED EMBODIMENTS AND OF MAKING AND USING THEM

A. Monoclonal Antibodies Which Bind to IgE-Expressing B Cells But Not Basophils Monoclonal antibodies and related products specific for the ige.bl epitopes bind to IgE on the surface of IgE-expressing B cells but do not bind to basophils. This differential binding of IgE-expressing cell types provides the basis for therapeutic and diagnostic uses for the antibodies.

It is crucial that the antibodies and related products of the invention do not bind to basophils and induce histamine release. Conventional anti-IgE antibodies will bind IgE on the surface of mast cells and basophils and trigger the release of pharmacologic mediators of allergy. The antibodies of this invention cannot bind IgE on these cells because the cognate epitope of IgE is masked and not available for binding. Thus, they do not induce the release of histamine or other allergic mediators from these cells.

The monoclonal antibodies and related products of this invention preferably do not bind to IgE bound to CD23, and/or will inhibit such binding. CD23 is the low affinity receptor for IgE on the surface of B cells, T cells, monocytes and eosinophils, and it is a receptor for the secreted form of IgE.

B. Therapy of IgE-Mediated Allergy Based Upon the Selective Elimination of IgE-Producing Cells The monoclonal antibodies and related products of this invention can be used to treat IgE-mediated allergy in humans or other mammals including, for example, rodents, dogs, cats and horses. A specific example of using a monoclonal antibody of the invention to reduce hypersensitivity in a mouse is described in detail below. The monoclonal antibodies and related products of the invention can also be used to reduce circulating IgE, selectively deplete IgE-expressing B cells, or as effector agents mediating an immune function, or as carder agents of toxins or cytotoxic cells. A specific example of using a monoclonal antibody of the invention to deplete circulating IgE in mice is described below.

Among the various immune functions that antibodies specific for surface antigens on target cells can mediate are antibody and complement-mediated cytolysis and antibody-dependent cellular cytotoxicity (ADCC). The antibodies may also mediate immune regulatory functions. Antibodies of certain IgG subclasses, such as mouse IgG2a and human IgG1 and IgG3, can mediate ADCC carded out by certain Fc receptor-bearing phagocytic leukocytes. For example, OKT3, a mouse IgG2a monoclonal antibody specific for human T cell surface antigen (which was the first monoclonal antibody product approved by the FDA for marketing as a therapeutic agent) is used in patients to provide rapid depletion of T cells in the blood and to induce an immunosuppressed state (for kidney transplantation). Russell, P. S. et.al, *Transpl. Proc.* 17:39–41 (1985). OKT3, at a dosage of 5 mg/day/subject, can completely deplete circulating T cells. The monoclonal antibodies of this invention, especially in the form of mouse gamma 2a antibodies or human or humanized antibodies bearing human gamma-1 or gamma-3 chains, can be used to deplete IgE-expressing B cells by the ADCC mechanism.

The monclonal antibodies of the invention can be administered as free antibodies to patients afflicted with IgE-mediated allergy in amounts sufficient to eliminate substantially IgE-producing cells and consequently, to deplete substantially IgE. Based on the results of a study with mice described below, the amount administered to humans can range from 30–500 mg/dose/subject. This amount was estimated by calculating the amount needed to deplete IgE in the mouse, and then multiplying by the ratio of a human's blood volume over that of a mouse. A similar calculation, where the ratio of blood volume is multiplied by the mouse dose administered, can be used to determine the amount of antibody which should be administered to a dog, cat, horse, or any other mammal.

The antibodies and related products of the invention can also be administered nasally. On the lining of nasal channel and respiratory tract are areas in which active mast cells are concentrated. The IgE-producing B cells and free IgE in the extravascular space of these tissues may have better accessibility to the mast cells than IgE-producing B cells and IgE in other parts of the body. It is possible that a nasal route of administration (e.g., by nasal spray) may be used to deliver relatively high concentrations of therapeutic products into these areas and thus to achieve speedier and more effective results. The antibodies and related products of the invention can also be administered ocularly.

For therapeutic uses in humans, human or humanized antibodies are preferred. Humanized antibodies can take several forms, including chimeric antibodies (having an animal variable region and a human constant region), or CDR-grafted antibodies, in which only the CDR regions are animal derived and have an amino acid sequence corresponding to the animal sequence, and substantially all of the remaining portions of the molecule are human derived and correspond in amino acid sequence to a human antibody. See Riechmann, L. et al., Nature 332:323–327 (1988); U.S. patent application No. 07/952,802 entitled "CDR-Grafted Anti-IgE Monoclonal Monoclonal Antibodies which Bind to IgE-Expressing B Cells but not Basophils" filed on Sep. 25, 1992 (abandoned), (incorporated by reference). Human antibodies can be made by using human immunoglobulin expression libraries (Stratagene Corp., La Jolla, Calif.) to produce fragments of human antibodies ($V_H$, $V_L$, $F_v$, Fd, Fab, or F(ab')$_2$), and using these fragments to construct whole human antibodies using techniques similar to those for producing chimeric antibodies. Human antibodies can also be made from certain individuals who have rheumatoid arthritis or autoimmune diseases and make antibodies against their own IgE molecules. Thus, it is possible that hybridomas or EBV-transformed B cell lines can be developed from the B cells of these patients. The antibodies of these hybrid or transformant cell lines are then screened for the specific binding to IgE on B cells and not on basophils.

As another alternative, one can create single peptide chain binding molecules in which the heavy and light chain $F_v$ regions are connected. See Huston, J. S. et al., Proc. Natl. Acad. Sci. USA 85:5879–5883 (1983). All of the wholly and partially human antibodies are less immunogenic than mammalian equivalents, and the fragments and single chain antibodies are also less immunogenic than mammalian equivalents. All these types of antibodies are therefore less likely to evoke an immune or allergic response. Consequently, they are better suited for in vivo administration than animal antibodies, especially when repeated or long term administration is necessary.

Immunotherapies employing the antibodies and related products of this invention may be used in combination with conventional desensitization immunotherapy. For example, desensitization with allergen may be performed in conjunction with the administration of anti-ige.bl antibodies or immunotoxins. One major effect of desensitization is that immunoglobulins of the IgG class are induced against the allergen/immunogen. The induction of an IgG response may be most effective when IgE-producing B cells are substantially depleted. The combination of antibody and desensitization therapy is attractive because it may lead to a longer lasting depletion of IgE-producing B cells.

C. Immunotherapy Combining an ige.bl-Specific Antibody and a Factor Enhancing ADCC Many factors, such as GM-CSF (granulocyte monocyte-colony stimulating factor), are known to induce the proliferation of leukocytes, including those mediating ADCC. In in vitro experiments, GM-CSF and M-CSF have been shown to augment the ADCC activity on tumor cells mediated by monoclonal antibodies specific for surface antigens expressed on the tumor cells. It is conceivable that the therapeutic effect of ige.bl specific monoclonal antibodies and related products can be enhanced by combining the use of factors that augment ADCC activities.

D. Immunotoxins Specific for IgE-Producing Cells

The ige.bl epitopes provide highly specific targets for immunotoxins directed against IgE-producing B cells. Immunotoxins specific for the epitopes bind to IgE-producing B cells but not to mast cells or basophils. In this way, IgE-producing B Cells can be selectively reduced or eliminated in a patient suffering from an IgE-mediated allergy. The reduction of the IgE producing cells reduces IgE levels in the circulation which results in a reduction of the amount of IgE available to bind mast cells and basophils. The immunotoxin does not kill mast cells or basophils and cause the release of pharmacologic mediators from these cells.

These immunotoxins can also be used diagnostically to determine the presence of or to quantify IgE or IgE-expressing B cells in a blood or serum sample. Such assays are similar in design to those used with antibodies without toxin conjugated thereto. In one embodiment, one would contact a population of cells with the immunotoxin and then assay for reactive cells by determining which are lysed by the immunotoxin, such as by counting the lysed cells under a microscope.

Immunotoxins for selective binding to IgE-producing lymphocytes are made of cytolytic or cytotoxic agents conjugated to a binding agent specific for an ige.bl epitope. The preferred specific binding agents are anti-ige.bl antibodies or fragments thereof (e.g., F(ab)'$_2$, Fab, $F_v$, or analogs or derivatives thereof). The cytolytic agents can be selected from any of the available substances including ricin, Pseudomonas toxin, diphtheria toxin, pokeweed antiviral peptide, trichothecenes, radioactive nuclides, and membrane-lytic enzymes. The antibody and the cytotoxin can be conjugated by chemical or by genetic engineering techniques.

The immunotoxins are administered to a patient afflicted with IgE-mediated allergy in amounts sufficient to reduce or to eliminate IgE-producing lymphocytes in the patient and thereby prevent or alleviate the symptoms of the IgE-mediated allergy. The immunotoxins may be used alone or in combination with free anti-IgE antibody.

E. Therapy With Bi-Specific Reagents

The antibodies of this invention can be used to target cytotoxic cells such as macrophages or cytotoxic T cells toward IgE-expressing B cells. The antibodies can be used to prepare bi-specific reagents having a specificity for a receptor of a cytotoxic cell and a specificity for IgE-expressing B cells (but not basophils). For example a hybrid antibody can be formed comprising two different Fab moieties, one Fab having antigen specificity for IgE-expressing B cells and not basophils, and the other Fab having antigen specificity for a surface antigen of cytotoxic cells, such as CD3 or CD8. The bi-specific reagent can be a bi-specific antibody (a single antibody having two specificities) or a heteroaggregate of two or more antibodies or antibody fragments. See, e.g., Reading, U.S. Pat. Nos. 4,474,893 and 4,714,681; Segal et al., U.S. Pat. No. 4,676,980.

F. Extracorporeal Treatment

While the ige.bl-specific monoclonal antibodies may be used for in vivo applications, they may also be used in extra-corporeal ex-vivo applications. The IgE in the circulation of allergic patients can be removed by an affinity matrix that is conjugated with the monoclonal antibodies of this invention. The ige.bl specific antibodies are superior to other antibodies that can induce histamine release from basophils and mast cells. Since anti-IgE antibodies may leak out from the affinity column, monoclonal antibodies specific for ige.bl can eliminate the concern and risk that the antibody could leak from the matrix and enter into the circulation of patients to cause an anaphylactic reaction or other adverse effects.

G. Removal of IgE by Anti-ige.bl Monoclonal Antibodies

In preferred embodiments, the monoclonal anti-IgE antibodies of this invention bind to an ige.bl epitope located at or near the FcεR binding site on IgE. In so doing, the antibodies block the binding site on IgE for mast cells and basophils. However, in order to achieve this, the antibodies must bind specifically to the epitope with an affinity which is greater than the affinity with which the FcεR binds to IgE. This inhibits IgE binding to FcεR. In addition, the immune complexes of IgE and the monoclonal antibodies may be removed rapidly by cells of the reticuloendothelial system. Upon intravenous injection of the monoclonal antibodies, most IgE molecules in the circulation will probably form immune complexes and be removed rapidly. These mechanisms will reduce the levels of free IgE in the body of the treated patient, whenever the therapeutic monoclonal antibodies are present in sufficient levels. These various mechanisms should contribute to the short term effects of the therapeutic antibodies. However, long-term therapeutic effects probably can be achieved without these mechanisms.

Affinity can be represented by the affinity or association constant, Ka. The Ka for IgE binding to the FcεR of mast cells and basophils has an estimated range of $1\times10^9-1\times10^{10}$ liter/mole. See Kulczycki, A., *New Trends in Allergy II,* ed. by Ring, J. and Burg, G., pp.25–32, Spring-Verlag, New York, 1986. Thus, a monoclonal anti-IgE antibody will effectively compete with FcεR if its affinity constant for IgE is in this range.

Mast cells and basophils in the body are bound with IgE. In most individuals, a large proportion of the FcεR are saturated by IgE. The IgE molecules have long half lives, with an "on" (receptor occupancy) time of about 20 hours. Kulczycki, A., *J. Exp. Med.* 140:1976 (1974). When the IgE molecules dissociates from the mast cells or basophils, the high affinity anti-ige.bl antibodies administered to the patient will tightly bind them and inhibit their reassociation with FcεR. Because IgE molecules have long "on" time and dissociate slowly from the basophils and mast cells, the therapeutic effects probably will be attained only a few days after the treatment (or even later) when a significant portion of the IgE on basophils and mast cells have dissociated from FcεR and have been complexed or cleared away by the anti-IgE antibody. When this is achieved, the density of IgE molecules bound to FcεR molecules on basophils and mast cells is substantially decreased and consequently, allergens are unable to cross-link sufficient numbers of FcεR to induce histamine release.

H. Diagnostic Uses for Antibodies and Related Products Which Specifically Bind to IgE-Producing Cells The antibodies and fragments, immunotoxins, and related products to ige.bl epitopes can be used to identify and enumerate IgE-expressing lymphocytes in mixed leukocyte populations. For this purpose, these products can be used in standard assay formats for determining cell surface antigens. In general, the product is contacted with a sample of the leukocytes to be tested under conditions which allow it to bind IgE-expressing cells in the sample. The cells are then examined for binding of product. This can be accomplished by conventional cell staining procedures. For example, a fluorescently labeled second antibody can be used to detect binding of the anti-IgE product.

I. Anti-Idiotypic Antibodies, Peptides and Methods of Active Immunization Against IgE The ige.bl-specific monoclonal antibodies described thus far can be used to generate paratope-specific, anti-idiotypic antibodies which offer another mode of treating IgE-mediated allergy. Antibodies against the paratope of the ige.bl-specific antibodies comformationally resemble the ige.bl epitope. These anti-idiotypic antibodies, or peptides with the sequence of the ige.bl epitopes, can be used to actively immunize against ige.bl and induce the endogenous formation of antibodies against the ige.bl epitope. The induced antibodies will mediate the same therapeutic effects as the anti-monoclonal antibodies and related products described above.

Paratope-specific, anti-idiotypic antibodies are administered to a patient suffering from IgE-mediated allergy in an immunogenic amount to induce the formation of ige.bl antibodies. The anti-idiotypic antibodies are preferably administered as humanized (chimeric or CDR-grafted) antibodies. They may also be given as antibody fragments (which also may be humanized) or analogues.

Another use for these anti-idiotype antibodies, or the synthetic peptides with the same sequence as the ige.bl epitopes, is in detecting the presence of the monoclonal antibodies of the invention in a fluid sample. This is useful for quantifying such monoclonal antibodies in a test reagent fluid, prior to using the antibodies themselves as diagnostic reagents to identify and enumerate IgE-expressing lymphocytes in a sample.

J. Production of the Monoclonal Antibodies of this Invention

The monoclonal anti-IgE and anti-idiotypic antibodies of this invention are produced by continuous (immortalized), stable, antibody-producing cell lines. The preferred antibody-producing cell lines are hybridoma cell lines, transfectoma cell lines, and myeloma cell lines. In principle, however, the cell lines can be any cells which contain and are capable of expressing functionally rearranged genes which encode the antibody variable regions of the antibody light and heavy chains. Preferably, the cell line should have the capability to assemble the chains into functional antibodies or antibody fragments. Thus, lymphoid cells which naturally produce immunoglobulin are most often employed. Transfectomas, which are viral or oncogenically transformed lymphoid cells, are also suitable.

Hybridoma cells which produce the anti-IgE antibodies of this invention can be made by the standard somatic cell hybridization technique of Kohler and Milstein, *Nature* 256:495 (1975) or similar procedures employing different fusing agents. Briefly, the procedure is as follows: the monoclonal anti-IgE antibodies are produced by immunizing an animal with human IgE, or peptidic segments of human IgE (secretory or membrane-bound), which are identified as potential components of ige.bl epitope. The peptides can be synthesized and conjugated to a carrier protein, such as keyhole limpet hemocyanin, to be used as immunogen. Lymphoid cells (e.g. splenic lymphocytes) are then obtained from the immunized animal and fused with immortalizing cells (e.g. myeloma or heteromyeloma) to produce hybrid cells. The hybrid cells are screened to identify those which produce the desired anti-IgE antibody.

The anti-IgE and anti-idiotypic antibodies can be produced in a rodent system and converted into chimeric rodent/human antibodies, or CDR-grafted antibodies, by the established techniques described in detail below. As explained above, these "near human" chimeric or CDR-grafted antibodies, or wholly human antibodies, are preferred for in vivo administration, especially where multiple doses are required.

For the production of the anti-IgE antibodies of this invention, human IgE for immunization can be purified from human serum. Alternatively, human IgE may be produced by culturing an IgE-producing cell line (for example, the cell line U266, ATCC number CRL8033). Human IgE is conjugated to a suitable matrix (such as cyanogen bromide-activated Sepharose 4B) to provide an IgE-specific immunoabsorbent. The IgE preparation can be contacted with the immuno-adsorbent which selectively adsorbs IgE. The adsorbed IgE can thereafter be eluted in substantially pure form from the immunoadsorbent.

In preferred embodiments, animals are immunized with a vigorous immunization protocol in order to produce a high frequency of lymphocytes producing IgE-specific antibodies. Spleen cells are obtained from the immunized animal and fused with an immortalizing cells, preferably myeloma cells which have lost the ability to secrete immunoglobulin. Many suitable myeloma cell lines are known in the art. An example is the murine myeloma NS-1. Fusion of the spleen cells and fusion partner can be carried out in the presence of polyethylene glycol according to established methods. Techniques of electrofusion may also be used. The resulting hybrid cells are clonally cultured and then screened for production of anti-IgE antibody.

Hybridomas producing antibodies which are specific for an epitope present on IgE-expressing B cells and absent on basophils and which have an affinity for IgE sufficient to block FcεR binding to IgE can then be selected. Hybridomas are first screened for production of antibody reactive with human IgE. This can be done by an enzyme-linked immunosorbent assay (ELISA) employing purified human IgE adsorbed to a solid phase.

One way of obtaining generally high affinity antibodies is as follows. The solid phase for the ELISA is coated with very small amounts of human IgE. For example, if a standard microwell plate is used as the solid phase, about 50 µl of a 0.1 µg/ml solution of IgE is used per well. Hybrids are selected which show a comparatively high enzyme activity (optical density level) in the assay. The culture supernatants contain either relatively higher amounts of antibodies or antibodies of relatively higher affinity or both.

Hybridomas are then screened for secretion of antibodies which do not react with basophil-bound IgE. A preferred method is to screen the antibodies for the inability to induce histamine release by basophils. The source of basophils for such histamine release assays is blood leukocytes from donors whose basophils are known to be very sensitive for induction of histamine release. An alternative and possibly less sensitive method is an immunofluorescence staining technique. Basophil leukocytes can be isolated from blood. Freshly isolated basophils have IgE on their surface. Monoclonal antibodies which do not bind basophil-bound IgE are specific for an epitope which is at or near a site occupied by the basophil FcεR, and hence is not accessible for binding by the monoclonal antibodies.

Hybridomas which produce paratope-specific anti-idiotypic antibody can be made by immunizing an animal with anti-IgE antibody and screening for antibodies which bind the paratope of the immunizing anti-IgE antibody. Immunization results in production of antibodies against the antigenic determinants on the anti-IgE antibody including the idiotype. Anti-idiotype antibodies are first screened for their binding to anti-IgE antibody and not other mouse antibodies. Those which are paratope-specific are screened on the basis of the antibody's ability to compete the binding of human IgE to the anti-IgE monoclonal antibody used for immunization.

Antibody fragments such as $F(ab')_2$, Fab and $F_v$ can be produced by standard techniques of enzyme digestion. In addition, synthetic peptides representing Fab and $F_v$ analogues can be produced by genetic engineering techniques. See e.g., Better, M. et. al. (1988) *Science* 240:1041; Huston, J. S. et al., (1988) *Proc. Natl. Acad. Sci. USA* 85:5879–5883; U.S. application Ser. No. 07/952,802, entitled "CDR-Grafted Anti-IgE Monoclonal Antibodies which Bind to IgE-Expressing B Cells but not Basophils" filed on Sep. 25, 1992 (abandoned) (incorporated by reference).

The chimeric anti-IgE antibodies include individual chimeric heavy and light immunoglobulin chains. The chimeric heavy chain is a contiguous polypeptide having a rodent (generally murine) heavy chain variable region or hypervariable regions and a human heavy chain constant region. The chimeric light chain is a contiguous polypeptide having a rodent light chain variable region and a human light chain constant region.

A CDR-grafted anti-IgE antibody is made by using recombinant DNA techniques to engineer gene sequences so that the complementarity-determining or hypervariable regions in the resulting antibody are of murine origin, and the majority of the remainder of the molecule is homologous to the human antibody. See e.g. Robert S. et. al. *Nature* 328:731–33 (1987); Better, M. et. al. *Science* 240:1041 (1988).

The chimeric or CDR-grafted antibodies can be monovalent, divalent or polyvalent. Monovalent antibodies are dimers (HL) formed of a heavy chain associated (through disulfide bridges) with a light chain. Divalent immunoglobulins are tetrameres ($H_2L_2$) formed of two associated dimers. Polyvalent antibodies can be produced, for example, by employing heavy chain constant region which aggregate (e.g., µ type constant regions).

The heavy chain constant regions of the chimeric or CDR-grafted antibodies can be selected from any of the five isotypes: alpha, delta, epsilon, gamma or mu. Heavy chains of various subclasses (such as the IgG subclasses) can be used. The different classes and subclasses of heavy chains are responsible for different effector functions and thus, by choosing the desired heavy chain constant region, chimeric antibodies with desired effector function can be produced. The light chain constant regions can be either kappa or lambda.

In general, the chimeric and CDR-grafted antibodies are produced by preparing a DNA construct which encodes each of the light and heavy chains components of the antibody. The construct includes a fused gene having a first DNA segment which encodes at least the antibody-binding portion of the variable region (e.g. functionally rearranged complementarity determining regions with joining segment) linked to a second DNA segment encoding at least a part of a human constant region. Each fused gene is assembled in or inserted into an expression vector. Recipient cells capable of expressing the gene products are then transfected with the genes. The transfected recipient cells are cultured and the expressed antibodies are recovered.

Genes encoding the variable region of rodent light and heavy chains can be obtained from the hybridoma cells which produce the anti-IgE antibodies. For example, the murine hybridoma cell lines which produce murine anti-IgE antibody provide a source of variable region genes.

Constant region genes and human framework region genes for CDR-grafting can be obtained from human antibody producing cells by standard cloning techniques. Alternatively, because genes representing the two classes of light chains and the five classes of heavy chains have been cloned, constant regions of human origin are readily available from these clones.

Preferably, the fused genes encoding the light and heavy chimeric chains are assembled into expression vectors which can be used to cotransfect a recipient cell. Suitable vectors for the gene constructs include plasmids of the types pBR322, pEMBL and pUC. Each vector contains two selectable genes—one for selection in a bacterial system and one for selection in a eukaryotic system—each vector having a different pair of genes. These vectors allow production and amplification of the fused genes in bacterial systems and subsequent cotransfection of eukaryotic cells and selection of the cotransfected cells. Examples of selectable genes for the bacterial system are the genes which confer ampicillin or chloramphenicol resistance. Examples of selectable genes for eukaryotes are gpt and neo.

The preferred recipient cell type is a myeloma cell line. Myeloma cells can synthesize, assemble and secrete immunoglobulins encoded by transfected antibody genes. Further, they possess the mechanism for glycosylation of the immunoglobulin. A particularly preferred recipient cell is the Ig-non-producing myeloma cell Sp2/0. Shulman et al., Nature 276:269 (1978). The cell produces only immunoglobulin encoded by the transfected immunoglobulin genes. Myeloma cells can be grown in culture or in the peritoneum of mice where secreted immunoglobulin can be obtained from ascites fluid. Other lymphoid cells such as B lymphocytes or hybridoma cells can serve as suitable recipient cells.

Lymphoid cells can be transfected with vectors containing immunoglobulin encoding genes in several ways, including by electroporation, protoplast fusion, or calcium phosphate precipitation. The resulting transfected cells provide continuous, stable cell lines which produce chimeric or CDR-grafted antibodies.

The invention is further illustrated by the following examples.

EXAMPLE I

Preparation of the Hybridomas and Monoclonal Antibodies a) Preparation of Human IgE:

Human IgE was obtained from a commercial source and purified for immunizing mice to obtain immune splenocytes for fusion and for screening hybrids. The IgE was also used to characterize the various monoclonal anti-IgE antibodies. Two preparations of human IgE were used. One was polyclonal IgE purified from human sera, which was obtained from Ventrex (Portland, Me.). This human IgE was purified from sera by affinity chromatography using Sepharose 4B column conjugated with rabbit IgG specific for human IgE. Contaminating human albumin and transferrin were removed with an affinity column conjugated with antibodies specific for albumin and transferrin. Monoclonal human IgE was also produced from culture supernatants of the IgE-producing U266 cell line. The IgE was affinity purified on a Sepharose 4B column conjugated with a monoclonal antibody specific for human IgE. This monoclonal antibody IgG was purified from the ascitic fluids of mice beating the specific hybridomas with a protein A-conjugated column.

The polyclonal and monoclonal human IgEs were analyzed by SDS-polyacrylamide gel electrophoresis under reducing and non-reducing conditions. In both cases, distinctive IgE molecules (under non-reducing conditions) and heavy and light chains (under reducing conditions) were observed and only traces of relatively light bands of some other contaminating proteins were present.

b. Immunization Procedure:

Male Balb/c mice of initially 6–8 weeks old were used for immunization for preparing immune spleen cells for fusion with myeloma cells to product hybrids. The polyclonal human IgE purified from sera provided by Ventrex was used as the immunogen. The rationale for using polyclonal IgE was that the monoclonal IgE produced by the U266 cell line might bear certain unknown anomalies. An additional purpose was to avoid generating monoclonal antibodies against the idiotypes of U266 IgE, because there would be a greater likelihood of induced anti-idiotypic responses against such monoclonal antibodies.

For immunization, each mouse was injected with 50 μg of human IgE per injection. The first immunization was given in complete Freund's adjuvant. The mice were injected subcutaneously at sites with high concentrations of lymph nodes, for example, the underside of the intersection of the limbs and the trunk. On month and two months later the mice received subcutaneous booster injections at the same sites with 50 μg IgE. The boosters were prepared essentially in the same manner as was the first injection, except that for the boosters the emulsification was done in incomplete Freund's adjuvant.

After at least another month, each mouse was reimmunized subcutaneously for the last time (the fourth injection) with 50 μg IgE in PBS. Each mouse was injected subcutaneously at the intersection of each limb with the trunk, and intraperitoneally. Three days after the last injection, the mice were sacrificed and their spleens were removed. The spleen cells were then fused with myeloma cells by the following procedure.

c) Fusion:

Suspensions containing a five-to-one ratio of spleen cells to myeloma cells were prepared. The myeloma cells were NS-1 cells, which were conditioned to have a doubling time of about seventeen hours. They were used for fusion when in the log phase. The NS-1 cells were subcultured in bacteriological plates (100 mm) at a concentration of $6 \times 10^4$ cells/ml in 10 ml of Dulbecco's Modified Eagle's Medium (DMEM) containing 5% fetal bovine serum (FBS), 100 units/ml of penicillin, and 100 μg/ml of streptomycin. The medium was changed every three days. Some other cells were subcultured at $1.5 \times 10^5$ cells/ml in 10 ml of the same medium, and the medium was changed every two days.

The spleen cells were prepared by placing the spleen on a bacteriological pate (100 mm) and injecting 20 ml of calcium, magnesium free PBS (CMF-PBS) into both ends of the spleen to loosen up the spleen cells. The spleen cells were then transferred to a 50 ml centrifuge tube.

The spleen cells were centrifuged at 100 g for five minutes, and then suspended in 5 ml of 0.83% $NH_4Cl$ (0.155M) for 10 minutes at room temperature to lyse the erythrocytes. 5 ml of CMF-PBS was added to the tube to stop the lysis. The cells were then pelleted and resuspended in 10 ml of CMF-PBS.

The concentration of lymphocytes was determined by adding 40 µl of cell suspension to 10 ml of saline together with 3 drops of Zap-oglobin™. The number of lymphocytes was counted with a hemacytometer and the concentration of cells determined.

The NS-1 cells were transferred from bacteriological plates (100 mm) to 50 ml centrifuge tube. The cell concentration was determined. The NS-1 cells were then suspended in 10 ml of CMF-PBS and mixed with spleen cells at 1:5 in a 50. ml centrifuge tube. Routinely, $2-5 \times 10^8$ cells from one immune spleen were obtained. Two spleens in each fusion experiment were used.

The cells were spun down and washed once with 10 ml of CMF-PBS. The supernatant was aspirated as much as possible with a glass Pasteur pipette. The tube was gently tapped to free the cell pellet.

Prior to preparing the cells, a fusion mixture had been prepared as follows. 5 g of polyethylene glycol 1450 (Kodak) had been mixed with 5 ml of CMF-PBS and 0.5 ml of DMSO. This mixture had been warmed to 56° C., titrated to a final pH of 7.0, and filtered through a 0.22 µMillipore filter to sterilize. 1.0 ml aliquot had been added to Cytotubes, and these had been stored at −70° C.

To prepare the fusion mixture for use, one of the aliquots in the Cryotubes was melted by heating it to 37° C. Separately, a tube containing 1.0 ml of DMEM (without serum) was heated to 37° C.

The 1.0 ml aliquot of polyethylene glycol fusion mixture was added to the cell suspension and the suspension was mixed well. Forty-five seconds after the polyethylene glycol fusion mixture had been added, 2.0 ml of the pre-heated DMEM (without serum) was added dropwise with mixing. The remaining 8 ml of the pre-heated DMEM (without serum) was then added. The cells were left at room temperature for 10 minutes.

2.0 ml of FBS was added to the suspension and the suspensions were mixed well. The combination of the FBS and the CMF-PBS can help to prevent adherence of cells to the test tube walls. The suspension was then centrifuged at 400 g for four minutes.

After spinning down, the cells were suspended in about 120 ml of a modified medium, supplemented with 5% FBS, 100 units/ml of penicillin, 100 µg/ml of streptomycin, and hypoxanthine, aminopterin and thymidine (HAT).

The concentration of the cell suspension was adjusted to $3.3 \times 10^5$ of the spleen cells per 200 microliters of suspension. 200 microliter aliquots of suspension were then distributed to each well of a 96 well microliter plate. Typically, 20-30 plates were prepared for each fusion. The plates were then transferred to an incubator and maintained at 37° C. in 5% $CO_2$.

The cells were grown for seven days in the plates, then the growth medium was withdrawn and new medium was added. Four days after that, an enzyme linked immunosorbent assay (ELISA) was performed on the antibodies in the wells to determine which would bind human IgE.

Four fusion experiments with mice using the above immunization protocols were done. For these fusions, 7, 15, 36, and 15 plates of 96 wells of fusion cells were prepared, respectively. More than 98% of wells had cell growth, with each well having on the average 3–5 clones of hybrids.

d. ELISA Procedure

ELISA with human IgE as the solid phase antigen was used as the primary screening procedure for the hybrids resulting from the fusion. The polyclonal IgE purified from human sera (Ventrex) was used as the antigen.

High affinity antibodies were selected by coating very small amounts of human IgE, 50 µl of 0.1 µg/ml, onto each well. Assuming all the IgE was bound to the solid phase, only 5 ng would be in each well. Because of this small amount, the possibility of screening out hybrids specific for contaminating proteins was also greatly reduced. Only wells that showed high O.D. readings were chosen for further characterization and for cloning.

In the procedure, 50 µl of 0.1 µg/ml of human IgE was added to the wells of a 96-well Immunlon I plates. The plates were covered and incubated for eighteen hours at 4° C. to allow the protein to bind to the plate.

The liquid contents of the plates were then emptied, and 200 µl of 0.1M $NH_4Cl$ was added to each well in order to saturate any remaining binding sites on the plates. The $NH_4Cl$ solution was left in the wells for 30 minutes at room temperature.

The $NH_4Cl$ solution was then removed and the wells were washed three times with PBS and 0.05% Tween 20. Some of the PBS/0.05% Tween 20 solution was left in the wells until the antibody suspension described below was added.

50 µl of the cell fusion supernatant from each well of the 96 well plates was added to each of the wells on the Immulon I plates and incubated for one hour. Following incubation, the plates were rinsed three times with PBS/ 0.05% Tween 20 in order to remove any unbound antibody.

The cell fusion supernatant would contain the antibody which was produced by the various hybridomas in the 96 well plates. The antibody which was specific to human IgE would bind thereto. The amounts of antibodies bound to the solid phase were then determined by a routine procedure using horseradish peroxidase-conjugated goat-anti-mouse IgG, using 3,3',5,5'-tetraethyl benzidine as the substrate.

From the approximately 7,000 well with were screened, about 4,000 wells (about 60%) were positive in the ELISA. From these 4,000 positive wells, 53 wells with the highest O.D. readings were chosen for cloning and further characterization.

The 53 monoclonal antibodies were checked in ELISA using plates having wells coated with human serum at various dilutions. All of them were negative in the ELISA suggesting that they did not react with human albumin, IgE, IgM, transferrin, or other major serum proteins which might have contaminated the IgE preparations used as the immunogen for mice, and as the antigen in the primary screening ELISA.

e) Single Cell Cloning:

Cell suspensions from each of the 53 wells with the highest O.D. readings in ELISA were expanded in the wells of a twenty-four well plate. The cell suspensions were diluted to thirty, fifty and one hundred cells per milliliter. 0.1 ml of the diluted cell suspensions (containing an average of three, five and ten cells, respectively) was placed into the wells of a 96-well plate. The wells had been coated with histone.

After the cells grew up to become colonies, the cells were checked under a microscope. The single-cell clones showing strongest reactivities in ELISA were chosen and expanded in culture.

f) Production and Purification of Monoclonal Antibodies:

To produce large quantities of desired monoclonal antibodies, the following procedure was performed.

Some of the clones showing high O.D. readings in ELISA, which were grown in the wells in the twenty-four well plates, were expanded further in 100 mm tissue culture plates. The expanded culture of the selected single-cell clones were then separately injected into the peritoneal cavity of pristine treated mice, using five million cells per mouse. After seven days the ascites fluid of each mouse was collected and frozen.

The monoclonal antibodies in the ascitic fluid were purified as follows. The frozen ascitic fluid was thawed and filtered through a nylon cloth to remove viscous material. Sufficient phenylmethyl sulfonyl fluoride was added to the ascitic fluid so that there was a final concentration of 0.1 mM. 0.05 ml of 1.2M acetate buffer (pH 4.0) was added for every milliliter of ascites fluid. The final concentration of the acetate buffer was 60 mM. The pH was adjusted to 4.5.

For every milliliter of treated ascites fluid, 25 µl of caprylic acid (MW of 144.21, density of 0.91 g/ml) was added dropwise with vigorous stirring. The suspension was kept at room temperature and stirred continuously for 30 more minutes.

The suspension was then centrifuged at 15,000 g for ten minutes in order to remove the precipitate. The supernatant, which contains IgG, was neutralized by adding a volume of 1M HEPES buffer (pH 8.0) equal to one-tenth the volume of the supernatant. The IgG was then precipitated with 50% $(NH_4)_2SO_4$.

The precipitate was then dissolved in HEPES saline buffer. This solution was dialyzed overnight against HEPES saline buffer in order to remove $(NH_4)_2SO_4$ from the IgG. The HEPES saline buffer was changed twice during the dialysis. After dialysis, the HEPES buffer saline contains purified dissolved IgG. The purified IgG was used in certain characterization assays.

Some monoclonal antibodies were purified from ascites or culture fluid by a dual column chromatography method. First, antibodies were chromatographed on DE-52 anion exchange resin (Whatman, Maidstone, England) using 0.05M Tris pH 8.0 with stepwise increments of NaCl from 0.01M to 0.15M. Antibody-containing fractions were identified by enzyme immunoassay, concentrated by Amicon filtration (Amicon, Danver, Mass., YM10 membrane) and purified further on a hydroxylapatite column (Bio-Gel HT; RioPad, Richmond, Calif.) using a 0.01 to 0.3M phosphate buffer (pH 7.4) step gradient. Purity was assessed by isoelectric focusing (13) and SDS-PAGE using the Pharmacia PHAST system (Pharmacia, Piscatway, N.J.) and the concentration determined by $OD_{280}nm$ (1.5=1 mg/ml).

EXAMPLE II

Characterization of the Monoclonal Antibodies of the Invention a) Binding to Basophils Using an Immunofluorescence Assay and a Radiobinding Assay:

The IgE-reactive monoclonal antibodies were studied to determine whether they bind to basophils isolated from peripheral blood. Initially, an immunofluorescence staining assay was used in this determination because basophils account for a small percentage (0.5–2%) of the total leukocytes.

1. Isolation of Basophils:

Basophils were highly enriched from the peripheral blood of normal, healthy individuals using density centrifugation on Percoll by adopting the procedure described by P. Raghuprasad, *J. Immunol.* 129:2128–2133 (1982). Briefly, Percoll stock solution was prepared by mixing 90 ml of 90% Percoll solution with 8.96 ml 10× Hanks-balanced salt solution, 0.45 ml 1N HCl, and 1 ml 10× HEPES buffer (pH 7.6). The required densities of Percoll were prepared by using the following formula (8): Percoll density (g/ml)= (% Percoll stock solution×0.001186)+1.0041, where 0.001186 is a constant and 1.0041 is the density of physiologic media. Because the density of Percoll is altered by temperature, it is prepared the day before the experiment and kept at room temperature overnight.

Heparinized blood freshly obtained from normal donors was diluted 1:1 with basic culture medium RPM1-1640 and centrifuged on a Ficoll/Hypaque cusion (density= 1.070 g/ml). The mononuclear cells at the interface were removed for other uses and the whitish layer on top of the red cell pellets was recovered. These granulocytes were washed and resuspended in basic medium and then centrifuged through two carefully layered Percoll gradients of 1.072 and 1.078 g/ml at 600×g for 15 minutes. The cells recovered at the interface of the Percoll layers and below the interface of basic medium/upper Percoll layer were harvested. These cells contained 2–10% of basophils, depending on the particular individual donors.

2. Assay Procedure:

50 µl of the enriched basophil suspension at a concentration of $5 \times 10^6$ cells/ml was added to several 1.5 ml microfuge tubes containing specific antibodies. 50 µl of the supernatants from the hybridoma clones showing the greatest O.D. readings in ELISA with human IgE as the antigen was then added to each tube. With some clones, repetitious assays were performed. When purified antibodies were available, they were used at 20, 5 and 1 µg/ml; when ascitic fluids were available, they were used at 1:50 dilutions.

The tubes with cells and antibodies were then incubated for 30 minutes at room temperature. After incubation, the tubes were spun, the supernatant was withdrawn, and the cells were washed two times with a mixture of RPMI 1640, containing 2% fetal calf serum and 0.1% sodium azide. The tubes were then tapped to loosen the cell pellet.

10 µl of labeled antibody, goat anti-mouse IgG conjugated with fluorescein isothiocyanate (FITC), was added to each test tube at a dilution of 1 to 200. This labeled antibody will bind to any monoclonal antibodies which have attached to IgE on basophils and provide a means for identifying these monoclonal antibodies.

The tubes were again incubated for 30 minutes at room temperature. The tubes were centrifuged, and the cells were washed with the same medium as before. The cells were then resuspended in 50 µl PBS, placed onto individual slides and cover-slipped. The cells were viewed with a fluorescence microscope.

For the antibody-stained cells, one could observe that some of cells in each viewing field were stained bright. The percentages of positively stained cells range from about 2–10%.

3. Radiobinding Assays:

Many of the steps used in a radiobinding assay are similar to those for immunofluorescence staining, described above.

The leukocyte fraction containing enriched basophils is incubated with the mouse monoclonal antibody and about 10,000 cpm of $^{125}$I-goat anti-mouse IgG in the presence of 1% normal goat serum as a blocker for non-specific binding. After 30 minutes, the incubation mixture is then overlaid on top of calf serum (100%) in a conical plastic centrifuge tube. After centrifugation to pellet the cells, the upper layer and the serum are removed. The tubes are inverted to drain the residual liquid. The tips of the cones containing the cell pellet are then cut off with a sharp razor blade. These tips are then placed in tubes and counted for $^{125}$I in a scintillation counter. The positive and negative binding is determined by comparing the amounts of bound $^{125}$I between negative control monoclonal antibody and the human IgE-specific monoclonal antibodies.

4. Results:

Initially, several experiments were performed using immunofluorescence assays. The tests were also repeated using similar procedures employing a biotin-labeled second antibody (goat anti-mouse IgG) and peroxidase-conjugated avidin. The results from the two assays indicated that the background staining varied from one antibody to another. The results also indicated that sensitivities of the assays are not better than those of the histamine release assays (described below). The major reason for the relatively lower sensitivities in these assays was that the percentages of basophils in the blood leukocytes were all low. Individuals with relatively high basophil percentage are preferred for these immunobinding experiments. Starting with leukocytes high in basophils, one can then prepare a basophil-enriched fraction which will be suitable for these experiments.

Binding of ige.bl-specific monoclonal antibodies and control antibodies to basophils purified from peripheral blood was determined at The Johns Hopkins University School of Medicine. In one experiment, 27% of the cell preparation were determined to be basophils by alcian blue staining. In the fluorescence flow cytometric analysis, a second antibody, FITC-goat-anti-mouse IgG was used. The control antibodies E10-100-9 and E10-95-3 stained a distinct population of 27% as indicated by a peak of high fluorescence intensity in the histogram. E101- 1, E11-4-70, E10-12-15 and E10-8-120 did not enhance to any extent the staining above the fluorescence profile established by using only the second antibody. These studies clearly indicate that the latter four antibodies do not bind to IgE on basophils and, thereby, do not induce histamine release from the basophils.

The cell line producing the monoclonal antibody E11-4-70 is deposited with the American Type Culture Collection, 12301 Parklawn Drive, Rockville, Md. 20852, under Accession No. HB 10595.

b) Induction of Histamine Release from Blood Leukocytes:

When a monoclonal antibody specific for human IgE binds to the IgE bound on basophils, it will cross-link the IgE and aggregate the underlying FcεR molecules and cause the release of histamine and other pharmacological mediators. The various human IgE-specific monoclonal antibodies were tested for the ability to induce histamine release from the washed human peripheral blood leukocytes.

1. Procedure:

The method employed was the same as described in detail by Siraganian and Hook. The in vitro assay quantiated the percentages of total histamine in the leukocyte population that was released into the culture medium upon the incubation with the release inducers. The determination of histamine in the medium or cell lysates was done with an automated instrument which extracted histamine with n-butanol and reacted it with a coupling compound, o-phthaldehyde, at high pH to form a fluorescent product, and measured the histamine released with a fluorometer.

Regarding the test procedure for histamine release from washed leukocytes, the procedure adopted was that described by Siraganian, R. P. and Hook, W. A. in *Manual of Clinical Chemistry*, ed. Rose, N. R. and Friedman, H., 2d Ed, pps 208–321, American Society of Microbiology, Washington, D.C. The blood was drawn from normal volunteers by venipuncture. In a 50 ml conical tube, each 10 ml blood was mixed with 1 ml 0.1M EDTA and 2.5 ml dextrandextrose solution. (All solutions and reagents mentioned here are described in detail by Siraganian, supra.) The mixture was allowed to settle at room temperature for 60–90 minutes until a sharp interface developed between the erythrocyte and plasma layers. The plasma-leukocyte-platelet layer was drawn off and spun at 1,100 rpm for 8 minutes at 4° C. The supernatants containing the platelets were removed and 2–3 ml solution of cold PIPES A-EDTA was added and the cells were resuspended. Another 40 ml of cold PIPES A-EDTA was added and the cells were spun down. After the supernatants were removed, the cells were resuspended in 20 ml PIPES A. The cells were then spun down again and resuspended in PIPES ACM at a cell density of $4 \times 10^6$/ml.

Tubes containing 0.3 ml of the washed leukocytes and tubes containing 0.3 ml of the culture medium of hybridomas were warmed up to 37° C. in 6 minutes. The tubes were mixed and incubated at 37° C. with shaking every 10 minutes. At the end of 60 minutes, the cells were spun down and the supernatants were saved. For total histamine content, 0.3 ml of the washed leukocytes were mixed with 6% perchloric acid.

2. Results:

The results of extensive studies using leukocytes known to release high amounts of histamine are summarized in Table I. The antibodies were diluted 100, 10,000, or 1,000,000 fold from ascitic fluid or purified antibodies (1 to 5 mg/ml). The result show that among the 41 monoclonal antibodies, 12 did not induce histamine release.

It was also examined whether E101-1 and E11-4-70 would or would not induce histamine when a second goat-anti-mouse IgG antibody was added into the culture. It was shown that the second antibody could enhance suboptimal concentrations of control antibodies E69-2, E10-100-9 to release histamine. However, under these condition, E100-1 and E11-4-70 still did not induce histamine release.

TABLE I

Reactivity with IgE-Expressing Cells and Ability to Induce Histamine Release by Basophils of Mouse Monoclonal Antibodies Specific for Human IgE

| Monoclonal Antibodies | Binding to SK007 Cell Flow Cytometry | Histamine Release Antibody Dilution $1/10^2$ $1/10^4$ $1/10^8$ (% of Total Release) | | |
|---|---|---|---|---|
| Group I | | | | |
| E101-1 (γ2a, κ) | + | 0 | 0 | 0 |
| E8-5-3 (γ2b, κ) | + | 0 | 0 | 0 |
| E10-21-15 (γ1, κ) | + | 0 | 0 | 0 |
| E10-8-120 (γ1, κ) | + | 0 | 0 | 0 |
| E10-12-55 (γ2a, κ) | + | 0 | 0 | 0 |
| E11-4-70 (γ2b) | + | 0 | 0 | 0 |

TABLE I-continued

Reactivity with IgE-Expressing Cells and Ability to
Induce Histamine Release by Basophils of
Mouse Monoclonal Antibodies Specific for Human IgE

| Monoclonal Antibodies | Binding to SK007 Cell Flow Cytometry | Histamine Release Antibody Dilution | | |
|---|---|---|---|---|
| | | $1/10^2$ | $1/10^4$ | $1/10^8$ |
| | | (% of Total Release) | | |
| Group II | | | | |
| E10-55-31 ($\gamma$1, $\kappa$) | − | 0 | 0 | 0 |
| E8-13-1 ($\gamma$1, $\kappa$) | − | 0 | 0 | 0 |
| E8-32-9 ($\gamma$1, $\kappa$) | − | 0 | 0 | 0 |
| E357-4 ($\gamma$1, $\kappa$) | − | 0 | 0 | 0 |
| E8-37-4 ($\gamma$1, $\kappa$) | − | 0 | 0 | 0 |
| E8-4-17 ($\gamma$1, $\kappa$) | − | 0 | 0 | 0 |
| Group III | | | | |
| E69-2 ($\gamma$1, $\kappa$) | + | 44 | 13 | 0 |
| E10-100-9 ($\gamma$2a, $\kappa$) | + | 68 | 45 | 0 |
| E10-41-16 ($\gamma$2a) | + | 95 | 91 | 91 |
| E10-95-3 ($\gamma$2b, $\kappa$) | + | 65 | 68 | 3 |
| E10-68-10 ($\gamma$1, $\kappa$) | + | 56 | 42 | 2 |
| E10-10-3 ($\gamma$1, $\kappa$) | + | 85 | 78 | 2 |
| E10-5-83 ($\gamma$1, $\kappa$) | + | 82 | 80 | 6 |
| E10-24-28 ($\gamma$2b, $\kappa$) | + | 79 | 89 | 5 |
| E10-27-5 ($\gamma$2b, $\kappa$) | + | 68 | 90 | 9 |
| E10-22-84 ($\gamma$2a, $\kappa$) | + | 77 | 84 | 15 |
| E10-74-28 ($\gamma$1, $\kappa$) | + | 60 | 65 | 3 |
| E10-1-88 ($\gamma$1, $\kappa$) | + | 72 | 55 | 2 |
| E10-3-14-25 ($\gamma$1, $\kappa$) | + | 68 | 58 | 3 |
| E10-7-19 ($\gamma$1, $\kappa$) | + | 38 | 26 | 6 |
| E10-18-3 ($\gamma$1, $\kappa$) | + | 33 | 26 | 0 |
| E10-40-62 ($\gamma$1, $\kappa$) | + | 37 | 24 | 9 |
| E10-19-12 ($\gamma$1, $\kappa$) | + | 28 | 37 | 36 |
| E10-52-38 ($\gamma$1, $\kappa$) | + | 57 | 64 | 14 |
| E10-54-26 ($\gamma$1, $\kappa$) | + | 34 | 17 | 2 |
| E235-6-($\gamma$1, {}) | + | 52 | 25 | 12 |
| E10-14-52 ($\gamma$1, $\kappa$) | + | 52 | 24 | 0 |
| E10-71-47 ($\gamma$1, $\kappa$) | + | 30 | 16 | 0 |
| E10-25-44 ($\gamma$2b, $\kappa$) | + | 31 | 26 | 0 |
| E10-61-6 ($\gamma$1, $\kappa$) | + | 81 | 78 | 70 |
| E10-33-22 ($\gamma$2a) | + | 77 | 74 | 16 |
| E608-10 ($\gamma$1) | + | 81 | 84 | 86 |
| E688-13 ($\gamma$1) | + | 86 | 91 | 90 |
| E10-80-4 ($\gamma$2b) | + | 85 | 92 | 90 |
| E545-4 ($\gamma$1, $\kappa$) | + | 24 | 3 | 0 | c) Binding of Monoclonal Antibodies to IgE-Secreting Myeloma Cells:

Some myeloma cells (which are tumor cells derived from immunoglobulin-secreting plasma cells) are known to express low levels of immunoglobulins on their surface, compared to those immunoglobulins on the surface of resting B cells. IgE molecules are bound to the surfaces of basophils (or mast cells) and B cells by two different mechanisms. IgE binds to basophils and mast cells via the interaction of Fc$\epsilon$R molecules on these cells and a certain site on the Fc of IgE. IgE is synthesized by B cells and retained on the surface by an additional segment on the C-terminal end of the constant heavy chain. As noted above, this anchoring segment is found only in the membrane-bound immunoglobulins and not in secreted forms of immunoglobulins.

Since IgE-expressing B cells are very few in the mononuclear leukocyte fraction and since the topographical and structural characteristics of membrane-bound IgE molecules are most likely the same on plasma cells, B cells or IgE-secreting myeloma cells, a useful model to study the binding of monoclonal antibodies to IgE-expressing B cells is the SK007 cell line, which is a myeloma cell line from the American Type Culture Collection. Tanox Biosystems, Inc. (Houston Tex.) has also developed a transfectoma, SE44, that is a mouse myeloma expressing on its cell surface and secreting chimeric IgE antibody, with a constant region of human origin and a variable region of mouse origin. The cell line SE44 was constructed by transfecting murine myeloma Sp2/0 with chimeric heavy and light chain genomic DNA, each comprising the constant regions of human $\epsilon$ and $\kappa$ immunoglobulins and the variable regions of a mouse monoclonal antibody, BAT123, specific for the envelope protein of human immunodeficiency virus. The cell line SE44 is also used for determining whether anti-human IgE monoclonal antibodies bind to membrane-bound IgE on B cells.

1. Procedure:

Human SKO-007, CCL-156 and CCL-159 cells, expressing surface-bound human IgE-lambda, IgM-lambda and IgG1-kappa, respectively, were maintained in RPMI-1640 medium supplemented with 5% fetal bovine serum and 2 mM glutamine from GIBCO and 1% antibiotic-antimycotic solution. Peripheral blood mononuclear cells obtained by venipuncture of healthy donors were prepared by Ficoll-paque (Pharmacia, Piscataway, N.J.) density gradient centrifugation. Binding of monoclonal antibodies to the cell surfaces was assessed using two types of assays: binding of antibodies to live cells followed by indirect fluorescent flow cytometric analysis; and, an enzyme-linked antibody assay with the cells attached to microliter plates.

Binding of antibodies to live cells was performed by first pelleting the cells by centrifugation at 300 xg for 5 minutes, washing maintenance media from the cells with PBS-BSA, and then resuspending the cells at $20\times10^6$ in PBS-B. Fifty $\mu$l of cell suspension was mixed with 50 $\mu$l of antibody at twice the stated concentrations (1–10 $\mu$g/ml) in PBS-B and kept on ice. After a 30 minute incubation, 2 ml of ice cold PBS-B was added to each tube, and the cells were collected by centrifugation at 300 xg for 5 minutes at 5° C. Supernatant was decanted, cell pellets were resuspended by vortexing, and the cells were washed once with an additional 2 ml of PBS-B. After collecting the cells by centrifugation, 20 $\mu$l of affinity purified goat F(ab')$_2$ anti-mouse IgG (H+L) (Boehringer Mannheim, Lot 52934, code 60529) diluted 1:20 in PBS-B was added to each tube. The tubes were incubated for 20 minutes on ice and washed with PBS-B as above. Finally, cell pellets were resuspended in 0.5 ml of 1% paraformaldehyde (Polysciences, Inc., Warrington, Pa.) in PBS. Cells were analyzed using a EPICS Profile (Coulter, Hialeah, Fla.) equipped with a 5W argon laser running at 488 nm, 0.6W at Cytology Technology, Inc. (Houston, Tex.). Fluorescence intensity was collected with a built-in logarithmic amplifier after gating on the combination of a forward light scatter and a perpendicular light scatter to discriminate viable cells.

The cell-bound enzyme-linked antibody assay was performed by binding MAbs to glutaraldehyde-fixed cells according to the method of Kennett, R. H. in *Monoclonal Antibodies*, eds. Kennett, R. H. et al., pp 376, Plenum Press, New York (1980). Poly-L-lysine (100 $\mu$l/well, 10 $\mu$g/ml in PBS) was added to flat bottomed microliter plates (Falcon #3072, Becton Dickinson Labware, Oxnard, Calif.). This solution was flicked out of the wells after 30 minutes at 22° C. and 50 $\mu$l of cells at $2.5\times10^6$ cells/ml of calcium and magnesium-free Dulbecco-modified PBS (GIBCO) was added to each well. Cells were deposited on the bottom of the wells by centrifugation at 300 xg for 5 minutes and the cells were fixed at 22° C. for 10 minutes by adding 50 $\mu$l of glutaraldehyde diluted to 0.25% in ice-cold PBS. Nonspecific binding sites were blocked by sequential incubation of 0.1M glycine-0.1% BSA in PBS (200 $\mu$l/well) followed by Blotto [5% non-fat dry milk (Carnation, LA, Calif.) in PBS with 1 g/L of thimerosal]. Blocking solutions were removed by gentle flicking of the plate. Cells were exposed to 50 µl/well of control or test monoclonal antibody in Blotto for 1 hour at 37° C. Unbound antibody was removed by flicking the plate and washing 6 times with 200 µl/well of PBS using a Transtar 96 pipetting device (Costar, Cambridge, Mass.). Subsequently, the cells were incubated with 50 µl biotin-labeled affinity-purified goat anti-mouse IgG (KPL, Gaithersburg, Md.) at 0.5 µg/ml in Blotto for 1 hour at 37° C. All wells were washed as above and horseradish peroxidase-streptavidin was added at 0.5 µg/ml in Blotto for 1 hour at 37° C. Unbound conjugate was removed by washing as above and 100 µl of TMB substrate was added. The plates were kept in the dark for 30 minutes at 22° C. and the reaction was stopped with the addition of 50 µl/well of 4N $H_2SO_4$. Optical density at 450 nm was measured using a Biotek microliter plate reader.

2. Results:

Among the 41 monoclonal antibodies tested with flow cytometric analyses, 35 were shown to stain SK007 cells. All of the 29 monoclonal antibodies which induced histamine release from basophils stained SK007 cells. Among the 12 monoclonal antibodies which did not induce histamine release, 6 stained and 6 did not stain SK007 cells (Table I). The results with enzyme immunostaining were the same as those with flow cytometric assays. Thus, in the group of monoclonal antibodies that have been analyzed, six fit the criteria that they do not bind to basophils and induce histamine release but that they do bind to IgE-producing B cells. As discussed earlier, Siraganian and his colleagues (Fed. Proc. 46:1346, (1987)) developed two mouse monoclonal antibodies (E14C5IB1 and E11AC3IIC) against human IgE that could inhibit binding of IgE to basophils. We obtained these two antibodies from Dr. Siraganian and showed that they bind to SK007 cells and do not induce histamine release from basophils.

d) Monoclonal Antibodies Specific for ige.bl Epitope Do Not Bind to IgE on Low Affinity IgE.Fc receptors (FcεRII, or CD23):

Many T cells, B cells, monocytes, and eosinophils express the low affinity IgE, Fc receptors (FcεRII), also known as the CD23 antigen on cell surface. For therapeutic anti-IgE antibodies, such as the ige.bl-specific monoclonal antibodies, it is important to determine whether they bind to IgE that is bound by CD23. Such a binding may cause certain unwanted complications. We have used fluorescence flow cytometric methods to analyze the binding of ige.bl-specific monoclonal antibodies to IgE bound by CD23 on a human B cell line, IM9, using a procedure described above for the fluorescence staining of SK007 cells.

1. Procedure:

In the experimental procedure, $1\times10^6$ IM9 cells were incubated with 10 or 50 µg/ml of human IgE at 37° C. or 4° C. for 1 hour. The cells were washed three times, and human anti-IgE-monoclonal antibodies (which were either one of the ige.bl-specific monoclonal antibodies or a control antibody) was added at 10 µg/ml. After 1 hour incubation, the cells were washed and further incubated with FITC-goat-anti-mouse IgG, and then fixed. The cells were then analyzed using fluorescence flow cytometry.

2. Results:

The IM9 cells were first checked with anti-Leµ 20 antibody (anti-CD23; from Becton Dickinson Immunochemicals, Mountain View, Calif.) and shown to express strong fluorescence, indicating the presence of a high density of CD23 on cell surface.

In repeated experiments, monoclonal antibodies E101-1 and E11-4-70 showed clearly negative binding to IM9 cells which had been pre-incubated with either blank medium or human IgE. The control antibody E10-100-9 could bind to IM9 cells that had been pre-incubated with IgE, but not IM9 cells that had been pre-incubated with medium. These results indicated that E101-1 and E11-4-70 do not bind to IgE bound to CD23. In one experiment examining all of the monoclonal antibodies that do not induce histamine release from basophils, the results suggested that all of these monoclonal antibodies did not bind to IM9 cells pre-incubated with human IgE.

e) Determining the Binding Affinity with Human IgE:

1. Principle and Procedure:

It is well known that the sensitivity of immunoassays depends on the affinities of the antibodies for the substances to be measured. In the case of a solid phase sandwich immunoassays using two monoclonal antibodies, one as the solid-phase adsorbent and one as the tracer, both of the affinities of the two monclonal antibodies for the antigen are important. The influence of antibody affinity on the performance of different antibody assays and the use of immunoassays for calculating antibody affinity have been systematically studied. Nimmo et al. J. Immunol. Met. 72:177–187 (1984); Muller J. Immunol. Met. 34:345–352 (1980).

For determining the affinity of a monoclonal antibody for an antigen, one can coat the antigen on the solid phase of an immunoassay, for example, the microliter wells of a 96-well ELISA plate. The affinity of a monoclonal antibody relative to that of a reference monoclonal antibody for the same antigen on the solid phase can be determined by comparing the two monoclonal antibodies in the immunoassay. The affinity or the association constant of the reference monoclonal antibody is known. The O.D. readout of the monoclonal antibody for which affinity is to be determined compared to that of the reference monoclonal antibody will indicate whether the affinity of that monoclonal antibody is greater or lower than that of the reference monoclonal antibody.

When a reference monoclonal antibody against IgE is not available, the analysis can be made against a reference monoclonal antibody specific for a different antigen. By coating the same molar amount of the antigen on the solid phase and making all other assay conditions and parameters identical, the relative affinity of the two monoclonal antibodies can be determined from the O.D. readouts.

In determining the affinities of several human IgE-specific monoclonal antibodies that bind to SK007 cells but do not induce histamine release from basophils, the binding of various monoclonal antibodies to human IgE was compared with that of a monoclonal antibody to human β-HCG, which affinity is known to be $1\times10^{11}$ liter/mole. In our assays, we coated 50 µl of 0.1 µg/ml of β-HCG or human IgE on the wells of an ELISA plate and titrated the anti-HCG monoclonal antibodies against the respective antigens on the solid phase. The procedure was in effect the same as described in the ELISA procedure in Example I. By using horseradish peroxidase-conjugated goat-anti-mouse IgG and the enzyme substrate, the titration curves were determined.

The affinity of monoclonal antibodies of interest can also be determined by $^{125}$I-labeled human IgE. The solutions of the antibodies and $^{125}$I-IgE of known concentrations are mixed and the mixture is allowed sufficient time (24 hours) for the binding to reach to equilibrium. The immune complexes are then swiftly removed by affinity adsorption using excess Sepharose 4B conjugated with goat-anti-mouse IgG.

The free $^{125}$IgE is washed off swiftly. From the proportions of free $^{125}$I-IgE and bound $^{125}$I-IgE, the association constant, Ka, of the monoclonal antibody can be calculated. This method is especially suitable for antibodies of high affinity.

2. Results:

The six monoclonal antibodies that do not induce histamine release from basophils and that bind to SK007 cells have been determined to have association constant, Ka, in the range of $3 \times 10^8$ to $5 \times 10^9$ liter/mole.

EXAMPLE III

An Animal Model for in vivo Anti-ige.bl Antibody Evaluation

The aim of the study described below is to evaluate the concept of using an anti-ige.bl antibody for depleting IgE and treating allergy in an animal model. A rat monoclonal antibody to murine IgE, which does not bind to murine basophils, was used to study the concept in mice, and the in vivo effect of this antibody on skin reactions and its effects on the immune response.

1. Preparing A Cell Line Secreting Rat Anti-Murine IgE MAbs:

RA25 rats were immunized with a mixture of purified murine monoclonal antibodies of immunoglobulin class IgE (IgE MAbs) composed of three different anti-phosphorylcholine (PC) IgE (designated aPC4-33, aPC12-3 and aPC71-130) as well as an anti-dinitrophenol IgE (designated aDNP 69-3).

A mixture of the four IgE MAbs (10 μg each) in complete Freund's adjuvant was injected intraperitoneally (i.p.) into rats, followed by an identical i.p. injection on day 14. Serum titres against IgE were determined and rats with the highest titre were boosted intravenously (i. v.) with the same mixture of the four IgE MAbs in PBS 4 days before the fusion.

2. Cell Fusion:

Cell fusion was accomplished using $10^8$ spleen cells of immunized rats and $3 \times 10^7$ cells from the mouse myeloma cell line Sp2/0-Ag14 in 1 ml of 50% polyethylene glycol (PEG 4000, Merck). After washing, the cells were resuspended in 300 ml of DMEM-Medium followed by the addition of fetal calf serum to a final concentration of 15%, and then $3 \times 10^6$ normal mouse peritoneal exudate cell were added. The cells were distributed in 48 well Costart plates and the cultures were fed twice weekly with standard HAT selective medium, then later with HAT medium, for 3 to 6 weeks. When growth of hybridoma cells became visible, the culture supernatants were screened for binding to murine IgE by ELISA.

IgE specific hybridomas were cloned by limit dilution. Selected clones were expanded in culture and injected i.p. into Balb/c nu/nu mice primed with pristane for ascites production of antibodies.

3. Selection of Hybridomas Secreting Rat Anti-Murine IgE Specific Antibodies by Sandwich ELISA:

ELISA microtitre plates were coated with various purified immunoglobulins by incubating 500 ng per well of either the four above mentioned murine IgE MAbs. Alternately, as controls, murine MAbs and myeloma proteins (Bionetics) of other immunoglobulin classes were used in 50 μl of 0.05M sodium bicarbonate buffer at pH 9.6, coated for 2 hours at 37° C. and 15 hours at 4° C. The control immunoglobulins included the following preparations: 3 different IgM (aPC 35-2-2, aPC 111-1, and MOPC 104E), 3 different IgGa (aPC59-D4, aPC 56-1, and MOPC 21), 3 different $IgG_{2a}$ (aPC 55-1-8, UPC 10, and RPC 5), 3 different $IgG_{2b}$ (aPC 28-1, MOPC 195, and MOPC 141), 3 different $IgG_3$ (aPC 61-1, J606, and J5606) and 2 different IgA (TEPC 15 and MOPC 315).

After washing with PBS, the remaining protein-reactive sites were saturated by incubation for 2 hours at 37° C. with 150 μl of PBS-Tween buffer (0.05% Tween 20 in PBS containing 0.2% $NaN_3$ and 1% BSA, pH 7.4) and the plates were washed with PBS. 100 μl of hybridoma culture supernatants and corresponding dilutions thereof were incubated for 2 hours at 37° C. and, after washing the plates, bound rat monoclonal antibodies were developed by incubation with 100 μl of a predetermined dilution of alkaline phosphatase-labelled goat IgG anti-rat immunoglobulin (Sigma), followed by washing. The amount of enzyme taken up was determined by incubation (30 minutes, 37° C.) with 100 μl of p-nitrophenyl phosphate (1 mg/ml in 10% diethanolamine buffer containing 0.5 ml of $MgCl_2$, pH 9.8) and measurement of the optical density of the reacted product at 405 nm ($OD_{405}$) using a Multiscan photometer (Flow Irvine).

Based on the results of the screening procedure, 6 hybridomas, designated 18-20, 46-48, 4A1-28, 4B3-39, 1-5 and 3-11, were selected for further studies. They were derived from 4 different fusions and secreted monoclonal antibodies with high binding reactivity to murine IgE and no significant crossreactivity to MAbs and myeloma proteins of other Ig isotypes. The selected MAbs are designated (in abbreviated form) 18-20, 46-48, 4A1-28, 4B3-39, 1-5 and 3-11.

4. Production, Isolation and Purification of the Rat Anti-Murine IgE Monoclonal Antibodies:

For ascites production, female Balb/c mice (Animal farm, Sisseln, Switzerland) were pretreated with 0.3 ml pristane oil (Aldrich) i.p. One to 3 weeks later, mice received a second injection of pristane (0.2 ml i.p.) and were simultaneously inoculated i.p. with $2 \times 10^6$ hybridoma cells in 0.2 ml PBS. After 8–10 days, the resulting ascites fluid was collected and the cells were removed by centrifugation at 800 xg.

Antibodies were purified first, by having the ascites fluid clarified by centrifugation at 50,000 xg for 1 hour. After removing the top layer containing lipids, the protein concentration was determined and adjusted to 10–12 mg/ml with PBS. IgG was precipitated with 47% saturated ammonium sulfate at 0° C. The pellet was dissolved, and dialyzed against 20 mM Tris-HCl buffer pH 7.9 containing 50 mM NaCl. The IgG fraction was purified by anion exchange chromatography on a column of DE52 diethylaminoethyl cellulose (Whatman). The sample was applied into 20 mM Tris-HCl pH 7.9 containing 25 mM NaCl, and eluted by a gradient of increasing sodium chloride concentration from 25 mM to 200 mM. MAbs were eluted around 80 mM NaCl. The peak fractions were dialyzed against PBS overnight at 4° C. and stored in aliquots at −40° C. Purity was assessed by SDS-PAGE, and was found to be greater than 95%.

5. Determination of the Isotype of the Rat Anti-Murine IgE Monoclonal Antibodies:

The immunoglobulin class and subclass of the rat anti-murine IgE MAb were determined by double diffusion in agarose, as described by Ouchtherlony, O.,*Methods of Immunological Analysis, Progress in Allergy* VI:30–154 (1962). MAb 4B3-39, MAb 1-5 and MAb 3-11 were of class $IgG_1$, MAb 46-48 is of class $IgG_{2a}$, and MAb 18-20 and MAb 4A1-28 were of class $IgG_2$.

6. Determination of Specific Histamine Release Induced by the Rat Anti-Murine IgE MAbs In order to determine which of the MAbs induce histamine release, rat basophilic leukemia RBL-2H3 cells were grown and then trypsinized and washed with a balanced salt solution. Cells were sensitized with IgE by adding 1 µg of the murine IgE MAb aPC12-3 (specific for PC) per $10^5$ RBL-2H3 cells and incubating at 37° C. for 30 minutes while rotating. The cells were washed in medium, adjusted to $10^5$ cells/50 µl and incubated for 15 minutes in a shaker water bath at 37° C. with 50 µl of 0.5 µg of the various anti-IgE MAbs, or PC-BSA (1 µg) as a positive control, or BSS for determination of spontaneous histamine release. For the determination of total histamine release, 50 µl of BSS were added and the tubes were heated for 15 minutes at 90° C. The tubes were centrifuged for 5 minutes at 3000×g.

The histamine concentration in the supernatant was then determined. 60 µl of SAM cocktail (10 µCi$^3$-S-adenosyl methionine (DuPont NEL 155H)) in 1 ml PBS and histamine-L-methyl-transferase) was added to 50 µl supernatant and incubated for 90 minutes at 37° C. 40 µl of 1.5 NHClO$_4$, then 40 µl of 10N NaOH, and 500 µl of isoamyl alcohol/toluol (ration 2:8) were added to the tubes, vortexed for 1 minute and then centrifuged at 190×g for 5 minutes. 300 µl of the organic phase containing the radiolabelled methyl histamine was mixed with 1 ml ethanol and 10 ml scintillation cocktail (1 liter toluol and 42 ml Liquiflor™, DuPont) and counted in a Tri-Carb™ liquid scintillation analyser. The measured radioactivity is proportional to the histamine release.

The antibody 1-5 was found not to induce any histamine release, and the ratio of its IgE-binding antibody over its histamine releases activity was over 100 fold higher than for other antibodies.

7. Binding of the Rat Anti-Mouse IgE MAbs to IgE-Expressing B Cells and to IgE-Sensitized Mast Cells The binding of the rat anti-mouse IgE MAbs to IgE-expressing B cell hybridomas and to IgE coated mast cells was determined by flow cytometric analysis. Hybridoma cells producing the IgE MAb aPC12-3 served as surface IgE-expressing B cells (sIgE$^+$ B cells) and cells of the rat basophilic leukemia cell line RBL-2H3 sensitized with the IgE MAb aPC12-3 were used as IgE coated mast cells. Staining was performed by incubating $10^6$ cells in 200 PBS buffer containing 0.2% NaN$_3$ and 5% FCS with 1–5 µg/ml of biotinylated rat anti-mouse IgE MAbs for 30 minutes at 4° C. After washing, the cells were resuspended in 200 µl RIA buffer containing 3 µl Avidin-FITC (Becton-Dickinson, No. 9011) for 30 minutes at 4° C., and then washed again. They were resuspended in 200 µl buffer and analyzed by flow cytometry (Ortho Diagnostic System 50 HH connected with 2150 computer).

The control anti-IgE 4A1-28 strongly stained both types of cells, whereas the antibody 1-5 only reacted with the IgE-expressing B cell hybridoma cells. Thus, the antibody 1-5 does not recognize IgE bound to the high affinity receptor for IgE (FcεRI). This experiment suggests that antibody 1-5 binds to a particular site on IgE which is involved in the interaction of IgE with FcεRI.

8. Inhibition of IgE Binding to Fcε Receptor I Bearing Mast Cells by the Rat Anti-Mouse IgE MAb 1-5:

The capability of rat anti-mouse IgE monoclonal antibodies to inhibit the binding of $^{125}$I-labelled mouse IgE to the Fcε receptor of PB3 mast cells was determined in an inhibition radio/binding assay to solid phase attached cells. Flat-bottomed polyvinyl chloride microtitre plates were coated with 50 µl of poly-L-lysine at a concentration of 20 µg/ml in PBS. After washing with PBS 3×10$^5$ PB3 mast cells (50 µl at 6×10$^6$/ml) were added to each well, gently centrifuged (600 rpm, 4 minutes), and then immersed in freshly prepared 0.25% glutaraldehyde in PBS at 4° C. and left for 5 minutes. With a slow flicking motion the glutaraldehyde was removed from the wells and the plates were then washed in three successive 1 liter PBS bath. Remaining protein-reactive sites were saturated by incubating plates for 1 hour at 37° C. with PBS containing 1% BSA and 0.2% NaN$_3$. After washing in PBS, 25 µl of dilutions of the anti-IgE monoclonal antibodies and 25 µl of $^{125}$I-labelled mouse IgE MAb aPC12-3 (40,000 cpm ca. 3 ng) were added to each well. The plates were gently shaken and incubated for 15 minutes at 37° C. and 1 hour at room temperature. After addition of PBS and removal of bulk radioactivity by aspiration, the plates were washed 4 times in 1 liter PBS baths and dried. The radioactivity in the wells was measured and the degree of inhibition was calculated in comparison to $^{125}$I-IgE binding to cells in the absence of anti-IgE MAb.

The antibody 1-5 inhibited IgE binding to the PB-3 mast cells with an IC$_{50}$ of 10 ng/well corresponding to 1.3×10$^-$9M. Thus, antibody 1-5 efficiently inhibited the binding of IgE to PB-3 mast cells.

9. Effect of Antibody 1-5 on Skin Reactions In Vivo:

The effect of antibody 1-5 on the induction of possible skin reaction was investigated in vivo in two situations. Various concentrations of the antibody 1-5 or control anti-IgE antibody 4B3-39 were injected subcutaneously into immunized mice which had an ongoing IgE response against BPO-KLH or into rats which received 18 hours before 0.5 mg of a mouse IgE antibody against PC. In immunized mice, 0.1 µg of the control anti-IgE antibody 4B3-39 induced a 1 cm skin reaction of medium colour intensity (as revealed by trypan blue) and 1 µg induced a strong colour reaction. On the other hand, antibody 1-5 even at 10 µg induced no detectable skin reaction. Similar results were observed in passively IgE sensitized rats. Thus, in contrast to conventional anti-IgE antibodies, antibody 1-5 does not induce a skin reaction in vivo.

Since the antibody 1-5 does not induce mast cell and basophil activation and furthermore inhibits IgE binding to these cells, it was of interest to analyze whether the antibody was able to prevent an IgE induced skin reaction in vivo. Rats were passively sensitized with 0.5 mg mouse IgE against BPO and two days later challenged intradermally (i.d.) with BPO-conjugated BSA. A strong skin reaction was revealed after i.v. injection of trypan blue. If rats were given 1 mg anti-IgE antibody 1-5 i.v. 4 hours prior to IgE sensitization, the skin reaction was prevented. On the other hand, and as expected, application of antibody 1-5 17 hours after IgE sensitization had no effect on the antigen induced skin reaction. These results demonstrate that antibody 1-5 is able to prevent the induction of an IgE mediated skin reaction in vivo, presumably by inhibiting IgE binding to FcεRI bearing cells. However if IgE had already bound to mast cells, the antibody 1-5 was no longer able to prevent the skin reaction.

10. Effect of Antibody 1-5 on In Vitro IgE Response:

In order to test the effect of antibody 1-5 on the in vitro mouse IgE response, different concentrations of the antibody were added to splenic B cells which were stimulated to immunoglobulin production by irradiated EL-4 mouse thymoma cells in the presence of mouse IL-4. In this system, IL-4 induced every second B cell to switch to IgE expression resulting in 3 µg/ml of IgE at day 7 of culture. IgE levels were reduced up to 80% even at 1 µg/ml Mab 1-5. This effect was IgE-isotype specific in that the expression of IgG1 antibodies were not significantly affected. Furthermore, the addition of normal rat IgG to these cultures had no effect on the immunoglobulin production by mouse B cells.

The ELISA used to detect IgE levels was insensitive to the presence of antibody 1-5. It is not possible to draw conclusions as to the cause of the observed inhibition of IgE production. For this reason, cultures were also analyzed by detecting the number of IgE-producing cells. IgE-producing cells were inhibited to the same extent as IgE in the supernatant, which indicates that antibody 1-5 inhibited the generation of IgE-producing cells. As a further control, antibody 1-5 was added at the end of culture, and this had no effect on the IgE production by B cells, indicating that the lowered IgE levels are not due to down-regulation of IgE production.

11. Effect on the Secondary BPO-KLH Induced Response:

The effect of the anti-IgE MAb 1-5 on the in vivo IgE response was tested in Balb/c mice which had been preimmunized twice with benzylpenicilloyl-conjugated KLH in aluminum hydroxide. After a rest period the mice were treated four times with 200 μg of anti-IgE antibody 1-5 at about the same time as booster immunizations were administered at one day before boosting (i.p.), on the day of boosting (i.v.), as well as 1 and 4 days after boosting (i.p.). The serum antibody titer was determined 14 days thereafter.

The BPO-specific IgE antibody level, which in the control group reached 50 μg/ml, was over 80% reduced as a consequence of the treatment. This reduction in anti-BPO serum IgE antibodies by the antibody 1-5 was specific, in the sense that normal rat immunoglobulin (NR) or an irrelevant monoclonal rat antibody (C) did not affect the IgE serum concentrations. Furthermore, serum IgG 1 anti-BPO antibodies, which showed a titer of over 1 mg/ml, were not affected by this treatment. However, based on these results, one cannot determine whether the antibody 1-5 inhibited responding B cells, or whether the reduction in IgE antibody level was solely due to complexation and clearance of serum IgE.

In order to test the effect of antibody 1-5 on IgE antibody producing B cells, spleen cells from the mice were analyzed for BPO-specific antibody producing cells (APC), as determined by the ELISA spot assay. It was determined that the number of IgE anti-BPO APC is very small (around $20/10^6$ cells), and shows a considerable variation. Thus, although antibody 1-5 treated mice showed a reduction of over 50% of IgE anti-BPO APCs, the difference is statistically not significant. On the other hand, the number of IgG1 anti-BPO APCs (around $275/10^6$ cells) was not reduced relative to the two control groups.

12. Effect on the Primary Response to *Nippostrongylus brasilienis*:

The i.p. injection of living larvae of the nematode parasite *Nippostrongylus brasilienis* into mice induces a pronounced polyclonal IgE response with serum IgE levels of up to 10 μg/ml. Mice were treated with different doses of the antibody 1-5 four hours after injection, and the serum IgE and IgG1 levels were determined on day 6. The injection of 20 μg of antibody 1-5 (at day 0 and day 2) resulted in a reduction of over 50% in serum IgE levels. Injection of 200 μg was required to achieve a nearly complete reduction of serum IgE levels. Serum IgG 1 levels were not affected, irrespective of the dose of antibody 1-5.

13. Effect on the Ongoing IgE Production in CAF1 mice:

The above experiments were performed in Balb/c mice, which, although they respond with high IgE levels, have a normal serum IgE background level. CAF1 mice normally express a high IgE serum level of about 350 ng/ml, similar to the levels seen in atopic human individuals. It was therefore of interest to analyze the effect of antibody 1-5 on the natural high IgE response in these CAF1 mice. Injection of 50 μg of antibody 1-5 i.p. on two consecutive days induced a partial reduction of serum IgE levels which lasted for about two weeks, whereas two applications of 200 μg of 1-5 antibody reduced the serum levels by about 90% for the 4 week period of analysis.

14. Effect on a Later Immune Response:

Since the effect of antibody 1-5 on serum IgE titers could last for several weeks, as seen in the IgE response of the CAF1 mice, it was of interest to analyze the effect of the antibody treatment on a later response. For this reason, mice which were preimmunized with BPO-KLH were treated several months later with 200 μg antibody 1-5 i.p. on day 0 and day 2. Half of them were reimmunized with BPO-KLH four weeks thereafter. The treated group mounted a good BPO-specific IgE response which, although somewhat reduced relative to that of the untreated mice, was quite similar to that of another group treated with an irrelevant control antibody. Furthermore, the total serum IgE levels of all three groups were similar. Moreover, the BPO-specific IgE and total IgE levels was similar in the three groups. Thus, treatment with anti-IgE antibody 1-5 does not affect an IgE response induced 4 weeks after such treatment.

15. Conclusions and Correlations to Humans:

In conclusion, the monoclonal rat anti-murine IgE antibody 1-5 does not induce anaphylactic reactions but does reduce circulating IgE in vivo. It also is specific for the IgE isotype and does not induce histamine release from IgE sensitized mast cells. It binds to IgE in solution and to IgE-expressing B cells, but does not bind to IgE-sensitized mast cells. It prevents binding of IgE to mast cells, but does not induce skin reaction in vivo. It prevents antigen induced skin reaction in vivo and inhibits the generation of IgE producing cells in vitro, but selectively reduces IgE expression during an immune response in vitro and in vivo. Analysis of the 1-5 antibody in vivo revealed that it did not induce detectable skin reactions in IgE sensitized mice (as opposed to conventional anti-IgE antibodies) and furthermore inhibited an antigen induced skin reaction if given before IgE application. However application of antibody 1-5 after IgE administration or induction of an IgE response did not inhibit antigen-induced skin reactions, as expected. Furthermore, it was shown in culture that addition of antibody 1-5 inhibited IgE production in an isotype-specific way (1 μg/ml resulted in over 60% inhibition), in that the number of IgE producing cells was reduced.

Application of antibody 1-5 to BPO-KLH primed mice resulted in over 80% inhibition of serum IgE antibody levels. On the other hand, IgG1 antibody levels were not affected. The effect on the serum level could, however, be the result of 1-5 induced clearance of circulating IgE, rather than B cell depletion.

The dose relation of antibody 1-5 on the inhibition of the in vivo serum IgE production was assessed in mice challenged with the parasite *Nippostrongylus brasiliensis* which is known to induce a strong primary IgE response. Application of two 20 μg injections of MAb 1-5 resulted in a partial reduction of serum IgE. Furthermore, serum IgE levels could be suppressed for 4 weeks after two injections of 200 μg antibody 1-5.

These dosages of the 1-5 anti-IgE antibody can be correlated to determine the approximate amounts of anti-IgE antibody which should be administered to a human being in order to reduce circulating IgE and down-regulate the IgE response against IgE-inducing antigens. A mouse has about 2–3 ml of blood, whereas a human being has about 5 liters of blood. It is known that human beings have lower titer of circulating IgE than mice. Therefore, lower doses of anti-IgE antibody might be equally effective. It was seen in mice that 20 μg of antibody 1-5, administered twice, resulted in a reduction of over 50% in serum IgE. This would correspond to a human dose of about 30 to 50 mg, to be administered twice. 200 μg of antibody 1-5, administered twice, reduced serum IgE levels by 90% over a four week period. This would correspond to a human dose of about 300 to 500 mg, to be administered twice. As discussed above, less may be appropriate for human administration.

It was seen in mice that prior administration of the 1-5 antibody prevented a skin reaction in rats which had been passively immunized with mouse IgE against the antigen BPO and injected with BPO conjugated to BSA. Control rats, which had been passively immunized with mouse IgE and injected with the antigen BSA, did show a strong skin reaction.

These results can be correlated to humans. Human hypersensitivities mediated by IgE, such as skin surface reactions against allergens or other types of allergic reactions such as hay fever, could also be prevented by administering antibodies which bind to human IgE-expressing B cells but not basophils. These results can also be correlated to other mammals, such as other rodents, dogs, cats or horses.

Equivalents

It should be understood that the terms and expressions used in the specification are exemplary only and not limiting, and that the invention is defined only in the claims which follow, and includes all equivalents of the subject matter of the claims.

What is claimed is:

1. A method of reducing circulating IgE in a mammal comprising administering to the mammal a monoclonal antibody having a human IgG1 or IgG3 constant region that binds to secreted IgE and to membrane-bound IgE on IgE-expressing B cells but not to IgE bound to basophils to an amount effective to reduce circulating IgE.

2. A method of treating an allergic reaction in a mammal comprising administering to the mammal a therapeutically effective amount of a monoclonal antibody having a human IgG1 or IgG3 constant region that binds to secreted IgE and to membrane-bound IgE on IgE-expressing B cells but not to IgE bound to basophils.

3. A method of reducing circulating IgE in a mammal comprising administering to the mammal a monoclonal antibody that binds to secreted IgE and to membrane-bound IgE on IgE-expressing B cells but not to IgE which is bound to the FcεRII receptor and not to IgE bound to basophils in an amount effective to reduce circulating IgE.

4. A method of treating allergic reactions in a mammal comprising administering to the mammal a therapeutically effective amount of a monoclonal antibody that binds to secreted IgE and to membrane-bound IgE on IgE-expressing B cells but not to IgE which is bound to the FcεRII receptor and not to IgE bound to basophils.

5. A method of reducing circulating IgE in a mammal comprising administering to the mammal an antibody that binds to secreted IgE and to membrane-bound IgE on IgE-expressing B cells but not to IgE which is bound to the FcεRII receptor and not to IgE bound to basophils in an amount effective to reduce circulating IgE.

6. A method of treating allergic reactions in a human comprising administering to the human a therapeutically effective amount of a monoclonal antibody having its complementarity determining regions of murine origin and human IgG1 or IgG3 constant regions and binding to secreted IgE and to membrane-bound IgE on IgE-expressing B cells but not to IgE bound to basophils.

* * * * *